US009119540B2

(12) United States Patent
Sharma et al.

(10) Patent No.: US 9,119,540 B2
(45) Date of Patent: Sep. 1, 2015

(54) METHOD AND SYSTEM FOR NON-INVASIVE ASSESSMENT OF CORONARY ARTERY DISEASE

(75) Inventors: Puneet Sharma, Rahway, NJ (US); Bogdan Georgescu, Plainsboro, NJ (US); Viorel Mihalef, Keasbey, NJ (US); Terrence Chen, Princeton, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 636 days.

(21) Appl. No.: 13/226,779

(22) Filed: Sep. 7, 2011

(65) Prior Publication Data

US 2012/0072190 A1    Mar. 22, 2012

Related U.S. Application Data

(60) Provisional application No. 61/383,478, filed on Sep. 16, 2010, provisional application No. 61/384,382, filed on Sep. 20, 2010.

(51) Int. Cl.
*A61B 5/026* (2006.01)
*G06T 7/00* (2006.01)
*G06F 19/00* (2011.01)

(52) U.S. Cl.
CPC .............. *A61B 5/026* (2013.01); *G06T 7/0016* (2013.01); *G06F 19/321* (2013.01); *G06F 19/3437* (2013.01); *G06F 19/3468* (2013.01); *G06T 2207/10081* (2013.01); *G06T 2207/10096* (2013.01); *G06T 2207/10116* (2013.01); *G06T 2207/30048* (2013.01); *G06T 2207/30104* (2013.01)

(58) Field of Classification Search
None
See application file for complete search history.

(56) References Cited

U.S. PATENT DOCUMENTS

| | | | | |
|---|---|---|---|---|
| 7,127,095 | B2 * | 10/2006 | El Fakhri et al. | 382/128 |
| 7,134,994 | B2 * | 11/2006 | Alpert et al. | 600/481 |
| 7,693,315 | B2 * | 4/2010 | Krishnan et al. | 600/481 |
| 7,860,290 | B2 * | 12/2010 | Gulsun et al. | 382/131 |
| 7,912,528 | B2 * | 3/2011 | Krishnan et al. | 382/128 |
| 7,953,266 | B2 | 5/2011 | Gulsun et al. | |
| 8,315,812 | B2 * | 11/2012 | Taylor | 600/504 |
| 8,386,188 | B2 * | 2/2013 | Taylor et al. | 702/19 |
| 8,609,066 | B2 * | 12/2013 | Rosenmeier | 424/9.1 |
| 2008/0101676 | A1 | 5/2008 | Zheng et al. | |
| 2008/0262814 | A1 | 10/2008 | Zheng et al. | |
| 2009/0123050 | A1 | 5/2009 | Ionasec et al. | |
| 2009/0154785 | A1 | 6/2009 | Lynch et al. | |

(Continued)

OTHER PUBLICATIONS

Taylor, C.A. & Figueroa, C.A. "Patient-Specific Modeling of Cardiovascular Mechanics" Annu. Rev. Biomed. Eng., vol. 11, pp. 109-134 (2009).*

(Continued)

*Primary Examiner* — Kamini S Shah
*Assistant Examiner* — Jay B Hann (57) ABSTRACT

In order to assess coronary artery disease from medical image data, an anatomical model of a coronary artery is generated from the medical image data. A velocity of blood in the coronary artery is estimated based on a spatio-temporal representation of contrast agent propagation in the medical image data. Blood flow is simulated in the anatomical model of the coronary artery using a computational fluid dynamics (CFD) simulation using the estimated velocity of the blood in the coronary artery as a boundary condition.

28 Claims, 6 Drawing Sheets

(56) References Cited

U.S. PATENT DOCUMENTS

| | | | |
|---|---|---|---|
| 2010/0067760 | A1 | 3/2010 | Zhang et al. |
| 2010/0070249 | A1 | 3/2010 | Ionasec et al. |
| 2010/0239147 | A1 | 9/2010 | Vitanovski et al. |
| 2010/0239148 | A1 | 9/2010 | Zheng et al. |
| 2010/0280352 | A1 | 11/2010 | Ionasec et al. |
| 2011/0060576 | A1 | 3/2011 | Sharma et al. |
| 2013/0132054 | A1* | 5/2013 | Sharma et al. .................... 703/9 |
| 2013/0246034 | A1* | 9/2013 | Sharma et al. ................. 703/11 |

OTHER PUBLICATIONS

Ponzini, Raffaele, et al. "Womersley Number-Based Estimates of Blood Flow Rate in Doppler Analysis: In Vivo Validation by Means of Phase-Contrast MRI" IEEE Transactions on Biomedical Engineering, vol. 57, No. 7, pp. 1807-1815 (Jul. 2010).*

Ponzini, R., et al. "Reliable CFD-based Estimation of Flow Rate in Haemodynamics Measures" (2006).*

Di Carli, Marcelo F. & Hachamovitch, Rory "New Technology for Noninvasive Evaluation of Coronary Artery Disease" Circulation, vol. 115, pp. 1464-1480 (2007).*

Frydrychowicz, Alex, et al. "Time-Resolved Magnetic Resonance Angiography and Flow-Sensitive 4-Dimensional MRI at 3 Tesla for Blood Flow and Wall Shear Stress Analysis" J. Thoracic & Cardiovascular Surgery, vol. 136, pp. 400-407 (2008).*

Definition of "Flow" from Dictionary.reference.com.*

Molloi, Sabee, et al. "Quantification of Volumetric Coronary Blood Flow With Dual-Energy Digital Subtraction Angiography" Circulation, vol. 93, No. 10, pp. 1919-1927 (1996) available at <http://circ.ahajournals.org/content/93/10/1919.full>.*

Yang et al., "3D Ultrasound Tracking of the Left Ventricles Using One-Step Forward Prediction and Data Fusion of Collaborative Trackers", CVPR 2008.

) Ionasec et al., "Patient-Specific Modeling and Quantification of the Aortic and Mitral Valves from 4D Cardiac CT and TEE", IEEE Transactions on Medical Imaging, 2010.

Ionasec et al., "Robust Motion Estimation Using Trajectory Spectrum Learning: Application to Aortic and Mitral Valve Modeling from 4D TEE", Proceedings of 12th IEEE International Conference on Computer Vision, 2008, pp. 1601-1608.

S. Mantero, et al., "The Coronary Bed and its Role in the Cardiovascular System: A Review and an Introductory Single-Branch Model", Journal of Biomedical Engineering, vol. 14, Issue 2, Mar. 1992, pp. 109-116.

* cited by examiner

METHOD AND SYSTEM FOR NON-INVASIVE ASSESSMENT OF CORONARY ARTERY DISEASE

This application claims the benefit of U.S. Provisional Application No. 61/383,478, filed Sep. 16, 2010 and U.S. Provisional Application No. 61/384,382, filed Sep. 20, 2010, the disclosures of which are herein incorporated by reference.

BACKGROUND OF THE INVENTION

The present invention relates to modeling the cardiovascular circulation using medical images, and more particularly, to non-invasive patient-specific assessment of coronary artery disease based on 4D medical image data and numerical simulations.

Cardiac disease is the leading cause of death for men and women in the United States and accounts no less than 30% of deaths worldwide. Although medical advances in recent years have provided important improvements in the diagnosis and treatment of complex cardiac diseases, the incidence of premature morbidity and mortality is still large. One reason for this is a lack of accurate in-vivo and in-vitro estimates of patient-specific parameters that accurately characterize the anatomy, physiology, and hemodynamics, all of which play an important role in the progression of cardiovascular diseases.

Medical imaging based techniques (e.g., computed tomography (CT), angiography, etc.) are typically used in clinical practice for characterizing the severity of stenosis in the coronary arteries. However, such techniques only provide an anatomical assessment, which is often inadequate for clinical decision making. In particular, anatomical assessment of the severity of coronary artery stenosis often leads to overestimation or underestimation, both of which are undesirable. Overestimation of stenosis severity can lead to unnecessary intervention and subsequent risk of restenosis, while underestimation will likely lead to non-treatment. An accurate functional assessment may require measurements of pressure and/or flow, which are determined invasively.

BRIEF SUMMARY OF THE INVENTION

The present invention provides a method and system for non-invasive patient-specific assessment of coronary artery disease based on 4D medical image data. In particular, embodiments of the present invention provide flow and pressure measurements using a non-invasive Computational Fluid Dynamics (CFD) based method that uses patient-specific boundary conditions derived from 4D medical image data. Embodiments of the present invention also provide a non-invasive method for measuring the coronary flow reserve (CFR) of a patient based on 4D medical image data.

In one embodiment of the present invention, an anatomical model of a coronary artery is generated from medical image data. A velocity of blood in the coronary artery is estimated based on a spatio-temporal representation of contrast agent propagation in the medical image data. Blood flow is then simulated in the anatomical model of the coronary artery using a computational fluid dynamics (CFD) simulation using the estimated velocity of the blood in the coronary artery as a boundary condition.

In another embodiment of the present invention, a first sequence of medical image data acquired during rest and a second sequence of medical image data acquired during hyperemia are received. A first anatomical model of a coronary artery is generated from the first sequence of medical image data and a second anatomical model of the coronary artery is generated from the second sequence of medical image data. Maximum velocity of blood in the coronary artery during the resting state is estimated based on a spatio-temporal representation of contrast agent propagation in the first sequence of medical image data and a maximal hyperemia velocity of blood in the coronary artery is estimated based on a spatio-temporal representation of contrast agent propagation in the first sequence of medical image data. To determine the blood flow rates, the maximum velocity during resting state is mapped to an average velocity during resting state and the maximum velocity at hyperemia is mapped to an average velocity at hyperemia. The coronary flow reserve for the coronary artery is calculated based on the resting flow rate and the flow rate during hyperemia.

These and other advantages of the invention will be apparent to those of ordinary skill in the art by reference to the following detailed description and the accompanying drawings.

DETAILED DESCRIPTION

The present invention relates to non-invasive assessment of coronary artery disease using patient-specific modeling of the heart from a sequence of volumetric data, such as computed tomography (CT), magnetic resonance imaging (MRI), and echocardiography data. Such sequences of volumetric data, also referred to herein as 4D image data or 4D images, are sequences taken over a period of time to cover one or more cardiac cycles, in which each frame is a 3D image (volume). Embodiments of the present invention are described herein to give a visual understanding of the coronary artery disease assessment method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

CFD techniques based analysis for functional assessment of coronary diseases are typically based on simplified geometries of the coronary, with generic boundary conditions derived from population-wide data. This makes such techniques unsuitable for a comprehensive patient-specific assessment of a coronary artery disease, such as an assessment of stenosis severity in the case of coronary artery stenosis. However, in an embodiment of the present invention, a non-invasive CFD-based method uses patient-specific boundary conditions for both the flow and geometry, derived from medical image data, such as high resolution CT data.

Embodiments of the present invention provide a method and system for non-invasive functional coronary artery disease assessment based on 4D medical image data, such as high-resolution CT data, coupled with an underlying patient-specific hemodynamic analysis using computational fluid dynamics (CFD) modeling and simulations. In order for the underlying hemodynamic analysis to generate patient-specific parameters to be used for functional assessment, a 4D (3d+time) patient-specific geometric model for the coronary arteries of interest is determined from the medical image data. An image based analysis of the propagation of a contrast agent, via a spatio-temporal representation of contrast agent propagation, is performed to robustly recover the velocity profile over time on the coronary artery of interest. Patient-specific CFD simulations are performed in the coronary artery of interest, with inlet boundary conditions determined by the velocity profile derived from the contrast agent propagation, and hemodynamic parameters are derived from the CFD simulations to characterize the degree of stenosis.

Figure 1:
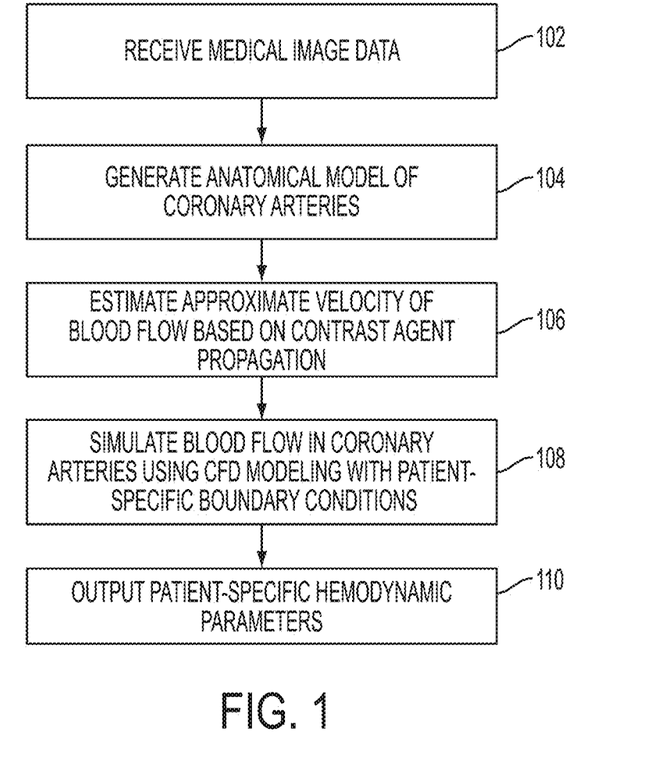
FIG. 1 illustrates a method for patient-specific assessment of coronary artery disease according to an embodiment of the present invention.

FIG. 1 illustrates a method for patient-specific assessment of coronary artery disease according to an embodiment of the present invention. The method of FIG. 1 transforms image data representing a coronary region of a patient into a patient-specific anatomical model of the coronary arteries and uses the patient-specific coronary artery model to simulate blood flow in the coronary arteries the heart.

Figure 2:
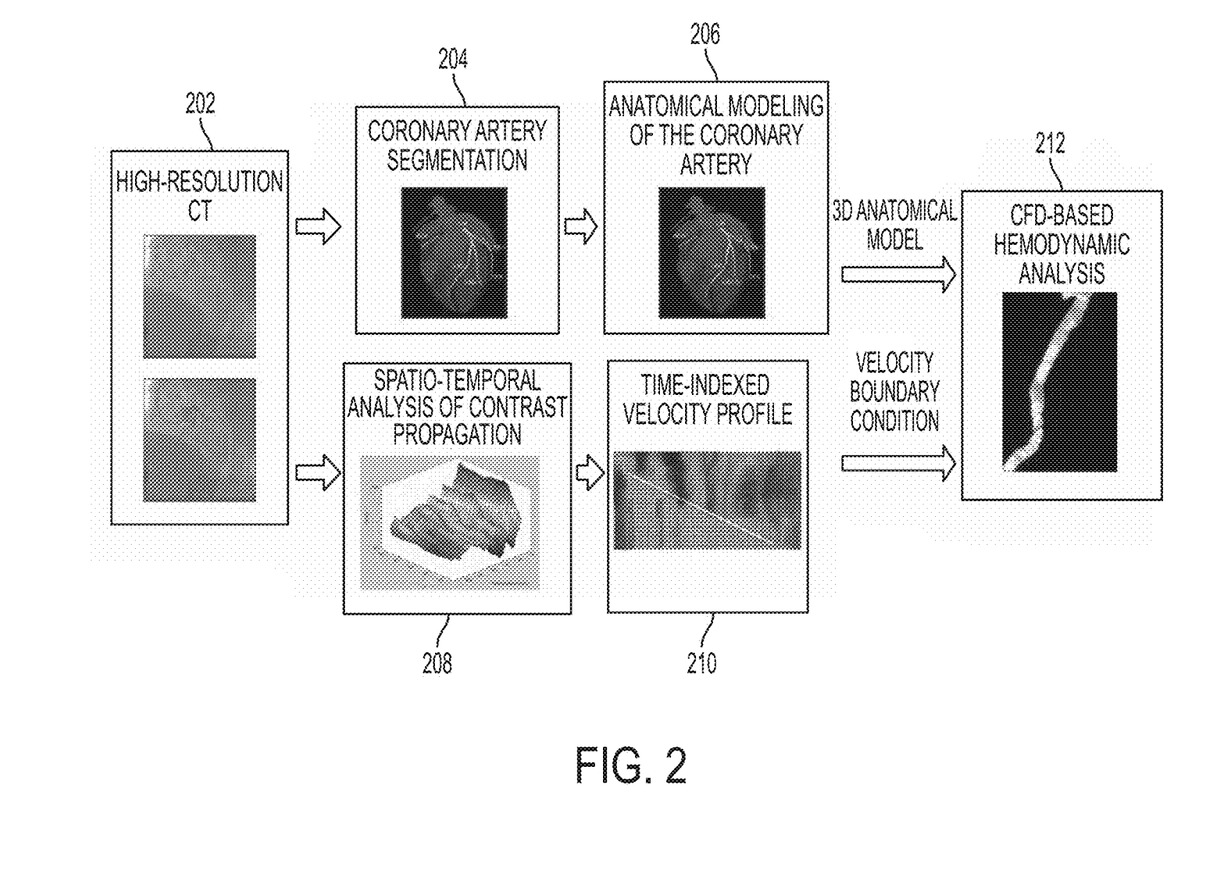
FIG. 2 illustrates exemplary results of the steps of the method of FIG. 1.

Referring to FIG. 1, at step 102, medical image data is received. In particular, at least one sequence of image data is received. The sequence of image data can be a sequence of 3D images (volumes) acquired over a certain time period. For example, such 4D image data (3D+time) can be acquired over a one full heart cycle. One or more sequences of image data can be received using various medical imaging modalities. For example, according to various embodiments of the present invention, a sequence of 3D CT data, 2D dynamic angiography data, and/or rotational angiography data can be received, but the present invention is not limited thereto. The image data can be received directly from one or more image acquisition devices, such as a CT scanner or an X-ray device. It is also possible that previously stored image data be loaded, for example from a memory or storage of a computer system or some other computer readable storage medium. The sequence of medical images can show the propagation of a contrast agent through the coronary arteries. FIG. 2 illustrates exemplary results of the steps of the method of FIG. 1. As illustrated in FIG. 2, image 202 shows frames of a high resolution CT volume.

Returning to FIG. 1, at step 104, a patient-specific anatomical model of the coronary arteries is generated from the received medical image data. The patient-specific anatomical model is a 4D (3D+time) geometric model of the coronary arteries generated using the 4D medical image data. In order to generate the patient-specific anatomical model of the coronary arteries, coronary arteries of interest are segmented in each frame of the 4D image data. The coronary arteries of interest can be segmented in each frame using any coronary artery segmentation method. For example, the coronary arteries of interest can be segmented in CT volume using the method described United States Published Patent Application No. 2010/0067760, which is incorporated herein by reference. A geometric surface model is then generated for the segmented coronary arteries of interest in each frame. For example, methods for anatomical modeling of the coronary arteries are described in U.S. Pat. No. 7,860,290 and U.S. Pat. No. 7,953,266, both of which are incorporated herein by reference. This results in an anatomical model of the coronary arteries of interest that shows the anatomy of the coronary arteries changing over time. As shown in FIG. 2, image 204 shows the coronary artery segmentation and image 206 show the anatomical modeling of the coronary artery, resulting in a 3D anatomical model.

Returning to FIG. 1, at step 106 the velocity of the blood flow in the coronary arteries is estimated based on contrast agent propagation in the received medical image data. In particular, once the coronary tree segmentation has been generated, a spatio-temporal representation of contrast agent propagation is derived from time-intensity curves of the received medical image data. The spatio-temporal representation of the contrast agent propagation is used to recover the velocity profile over time on the coronary of interest.

Figure 3A:
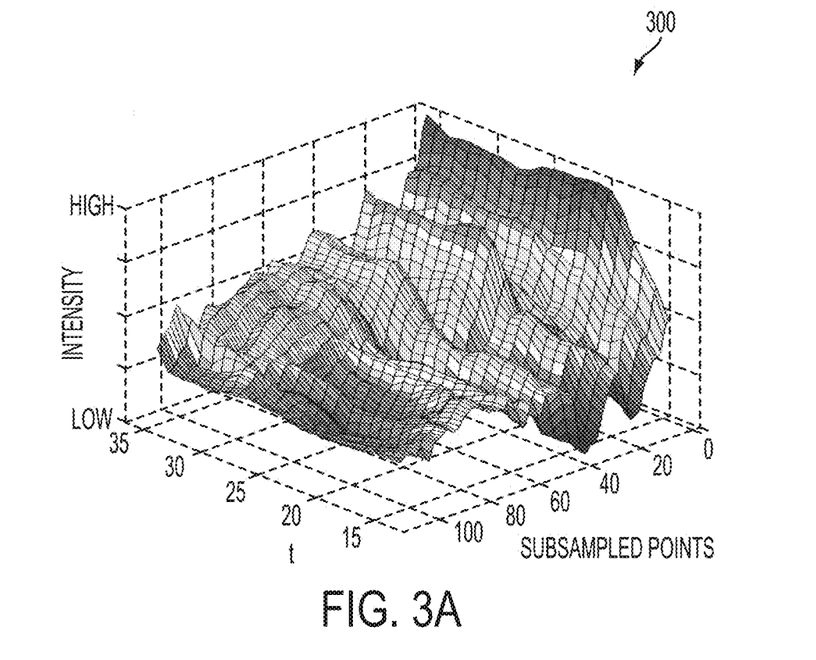
FIG. 3 illustrates velocity estimation based on a spatio-temporal representation of contrast agent propagation according to an embodiment of the present invention.
Figure 3B:
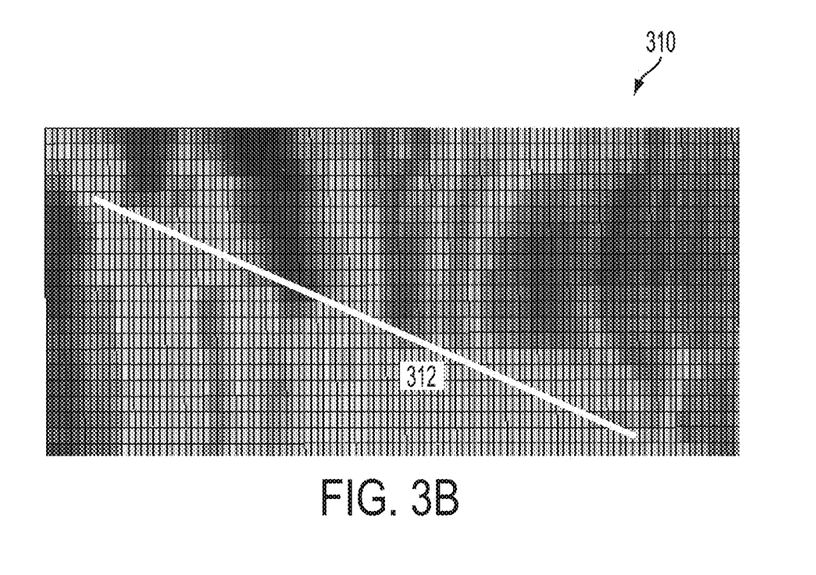

Spatio-temporal analysis of contrast propagation enables robust estimation of velocity profiles by integrating the available measurements of the intensity profile. FIG. 3 illustrates velocity estimation based on a spatio-temporal representation of contrast agent propagation according to an embodiment of the present invention. As illustrated in FIG. 3, image 300 show time-intensity curves for input 2D fluoroscopy images. The time-intensity curves of image 300 show the inverted intensity magnitude for points in the 2D fluoroscopy images over the length of a vessel over time. This information provides a spatio-temporal representation of the contrast agent propagation, as shown in image 310. A slope 312 is estimated for the spatio-temporal representation of the contrast agent propagation, and this slope 312 is a first order approximation of the velocity of the blood in the vessel. This approximation of the velocity can then be used to set the boundary conditions for the subsequent CFD modeling. Such an approximation of the velocity in a vessel can be performed for all coronary arteries of interest, resulting in an estimated velocity profile for the coronary arteries of interest. As shown in FIG. 2, images 208 and 210 show the spatio-temporal analysis of contrast propagation, which is used to generate the time-indexed velocity profile, resulting in a velocity boundary condition for the CFD modeling.

Returning to FIG. 1, at step 108, blood flow is simulated in the coronary arteries using CFD with patient-specific boundary conditions. In particular, the CFD modeling uses the coronary flow velocity profile estimated from the contrast agent propagation to set up boundary conditions for the CFD modeling. Blood is modeled as a Newtonian fluid, and the velocity field is obtained by numerically solving the discretized Navier-Stokes equations (continuity and momentum equations) under the rigid wall assumption. The discretized Navier-Stokes equations are used to incrementally simulate velocity of blood flow and pressure within the coronary arteries over time. The patient-specific anatomy of the coronary arteries are also input to the CFD modeling in order to constrain the blood flow simulations based on the patient-specific anatomy.

Several hemodynamic parameters have been proposed for functional assessment of coronary artery disease, such as flow rates and pressure drops for assessing the severity and stenosis, and wall-shear stress for plaque formations. However, such parameters were previously calculated based on simplified geometries of the coronary, with boundary conditions derived from population-wide data. According to an advantageous embodiment of the present invention, medical image data, such as high resolution CT data, is used not only to provide the anatomic model, but also to estimate patient specific boundary conditions for extracting these hemodynamic parameters via CFD simulations, and using these parameters for functional assessment of coronary artery disease. As shown in FIG. 2, image 210 shows the CFD-based hemodynamic analysis.

Returning to FIG. 1, at step 110, patient-specific hemodynamic parameters are output. The patient-specific hemodynamic parameters are calculated based on the CFD simulations. In particular, the CFD simulations result in simulated values for pressure and velocity of blood flow through the coronary arteries over time. These simulated values can be used to calculate various hemodynamic parameters, which can be used to assess coronary artery disease. For example, flow rates and pressure drops can be used for assessing the severity and stenosis, and wall-shear stress can be used for assessing plaque formations.

Another type of parameter used for functional assessment of coronary artery stenosis is flow reserve parameters, such as coronary flow reserve (CFR) and fractional flow reserve (FFR). CFR is defined as the ratio of maximal hyperemic flow in a coronary to the flow in the same coronary at rest. FFR is defined as the ratio of the maximal blood flow in the stenotic vessel to the maximal blood flow in a normal vessel, and is used to characterize the severity of stenosis. In clinical practice, pressure/flow based measurements are used to determine these flow reserves. Accordingly, according to an embodiment of the present invention, the method of claim 1 can be used to estimate these flow reserves.

According to an embodiment of the present invention, medical image data, such as high resolution CT data, can be used for anatomic modeling of the coronary, and for determining the maximum velocity based on contrast medium propagation. This is subsequently used for performing patient-specific CFD analysis, the results of which are used in a fitting procedure that maps the maximum velocity to an average velocity in order to determine the flow rates necessary for calculating CFR values.

Figure 4:
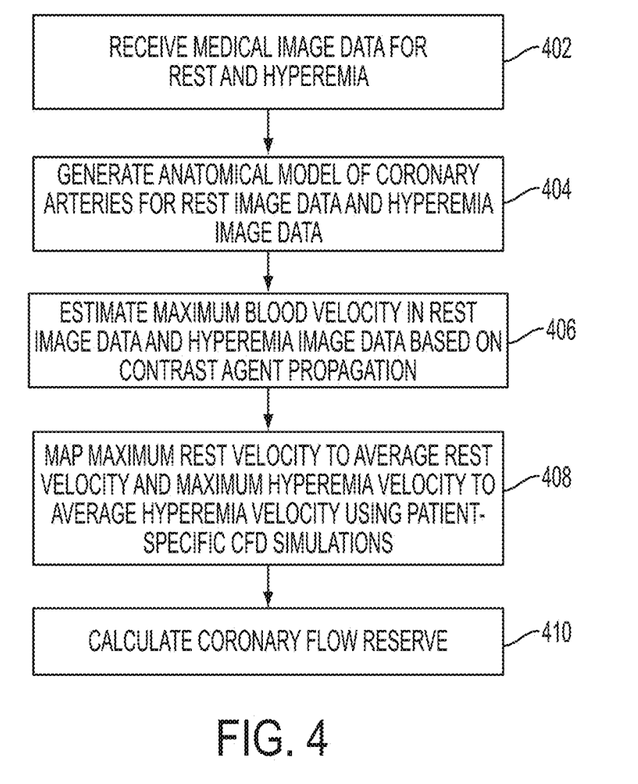
FIG. 4 illustrates a method of non-invasive assessment of coronary flow reserve based on medical image data according to an embodiment of the present invention.

FIG. 4 illustrates a method of non-invasive assessment of coronary flow reserve based on medical image data according to an embodiment of the present invention. As illustrated in FIG. 4, at step 402, medical image data is received for rest and hyperemia. In particular, a first sequence of image data that is acquired during rest is received and a second sequence of image data that is acquired during maximal hyperemic flow condition is received. These sequences of image data can be a sequences of 3D images (volumes) acquired over a certain time period. The sequences of image data can be acquired using various medical imaging modalities. For example, according to various embodiments of the present invention, sequences of 3D CT data, 2D dynamic angiography data, and/or rotational angiography data can be received, but the present invention is not limited thereto. The image data can be received directly from one or more image acquisition devices, such as a CT scanner or an X-ray device. It is also possible that previously stored image data be loaded, for example from a memory or storage of a computer system or some other computer readable storage medium. The sequences of medical images can show the propagation of a contrast agent through the coronary arteries.

At step 404, an anatomic model of coronary arteries of interest is generated for each of the received image sequences. It is to be understood that step 404 can be implemented similarly to step 104 of FIG. 1, as described above. At step 406, the maximum velocity is estimated for both the rest image data and the hyperemia image data based on contrast agent propagation. In particular, the maximum velocity for each sequence of image data can be estimated using a spatio-temporal representation of the contrast agent propagation, as described above in connection with step 106 of FIG. 1.

Figure 5:
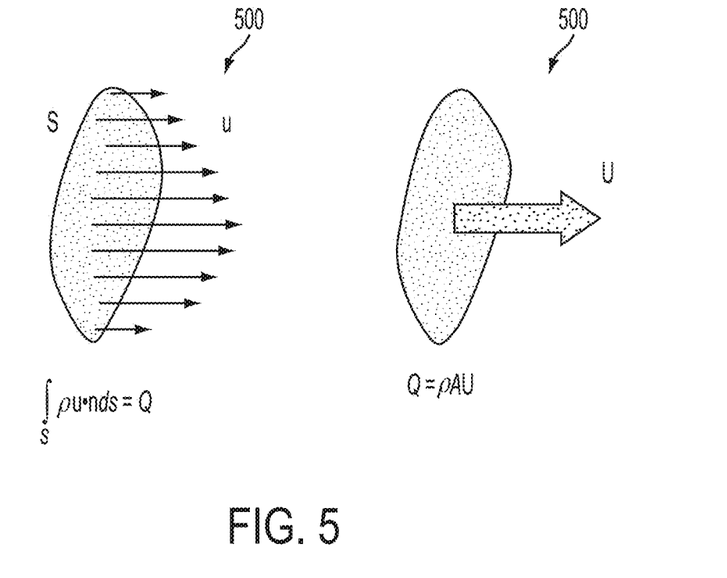
FIG. 5 illustrates determination of flow rate in a vessel from a velocity profile of the blood in the vessel.

At step 406, the maximum velocity at rest is mapped to an average rest velocity and a maximum velocity at hyperemia is mapped to an average hyperemia velocity using patient-specific CFD simulations. FIG. 5 illustrates determination of flow rate in a vessel from a velocity profile of the blood in the vessel. As illustrated in FIG. 5, for an accurate assessment of blood flow rate in a given vessel 500, velocity information u is needed on the entire cross-section S of the vessel 500. The blood flow rate Q can be determined by integrating the flow profile ρu (where ρ is the density the blood) over the surface area S. Accordingly, as illustrated in FIG. 5, the mass flow rate Q can also be determined as Q=ρAU, where U is the average blood velocity and A is the area of the cross-section S. Non-invasive blood velocity measurements record the maximum velocity $V_{max}$ on a given cross-section, thereby requiring assumptions on the velocity profile to determine the blood flow rate. In some cases, the flow rate is determined from the maximum velocity value by assuming a parabolic velocity profile. According to this criterion, the average velocity is determined as $0.5V_{max}$. However, this assumption does not take into account patient-specific geometry and hemodynamics.

Instead of making assumptions regarding the velocity profile of a vessel, CFD simulations can be used to obtain a more realistic relation mapping the maximum velocity $V_{max}$ to the average velocity $V_{avg}$. For small vessels, including coronary arteries, the following relation is used to map $V_{max}$ to $V_{avg}$:

$$V_{avg} = f(V_{max}, W) = V_{max} \frac{(1+pW^q)}{2}, \quad (1)$$

where W is the Womersley number, defined as $$W = R\sqrt{\frac{f\rho}{\mu}},$$

where f is the frequency of the pulsatile flow, R is the characteristic length scale (cross-sectional area of the coronary), ρ is the density, and μ the dynamic viscosity of blood.

The parameters p and q are determined using a fitting procedure, which uses data from a series of CFD simulations performed under defective boundary conditions, where instead of prescribing velocity profile boundary conditions, only flow values are specified. In particular, a series of CFD simulations are performed in which different flow rates are specified and the values for parameters such as W, f, R, ρ, and/or μ are varied. Each simulation results in a value for $V_{max}$ and a value for $V_{avg}$. Based on the values used for each simulation and the resulting values for $V_{max}$ and $V_{avg}$, the mapping parameters p and q are determined by fitting these parameters to the data resulting from the simulations. For example, these parameters may be fit to the data using a non-linear least squares fitting algorithm.

Once the mapping parameters p and q are determined based on the CFD simulations, the maximum velocity $V_{max}$ determined in step 404 can be mapped to an average velocity $V_{avg}$ using the Womersley number and the mapping parameters, as shown in Equation (1). This is performed separately for the rest image data and the hyperemia image data, resulting in an average rest blood velocity and an average hyperemia blood velocity.

At step 408, the CFR is calculated based on the average rest blood velocity and the average hyperemia blood velocity. In particular, the CFR can be calculated as:

$$CFR = \frac{Q_{hyp}}{Q_{rest}} = \frac{\rho A_{hyp} V_{hyp}}{\rho A_{rest} V_{rest}}, \quad (2)$$

where $V_{hyp}$ and $V_{rest}$ are the average velocity values derived from $$V_{avg} = V_{max} \frac{(1 + pW^q)}{2},$$

and $V_{hyp}$ and $V_{rest}$ are the cross-sectional areas of the coronary artery at hyperemia and at rest, respectively.

In the absence of the second sequence of medical images (i.e. images acquired during hyperemia), a similar method as presented above in FIG. 4, can still be applied. In such a case, the hyperemic blood flow analysis can be performed by using a different set of outlet boundary conditions (i.e. the boundary conditions modeling the flow characteristics of the coronary bed). Since most of the resistance to the flow in the coronaries is present in the microvascular circulation, the hyperemia condition is simulated by appropriately changing the resistance/impedance values in the outlet boundary conditions. Additional details on the resistance/impedance values appropriate to simulate the hyperemia condition are described in S. Mantero, et al., "The Coronary Bed and its Role in the Cardiovascular System: A Review and an Introductory Single-Branch Model", *Journal of Biomedical Engineering*, Volume 14, Issue 2, March 1992, Pages 109-116.

Figure 6:
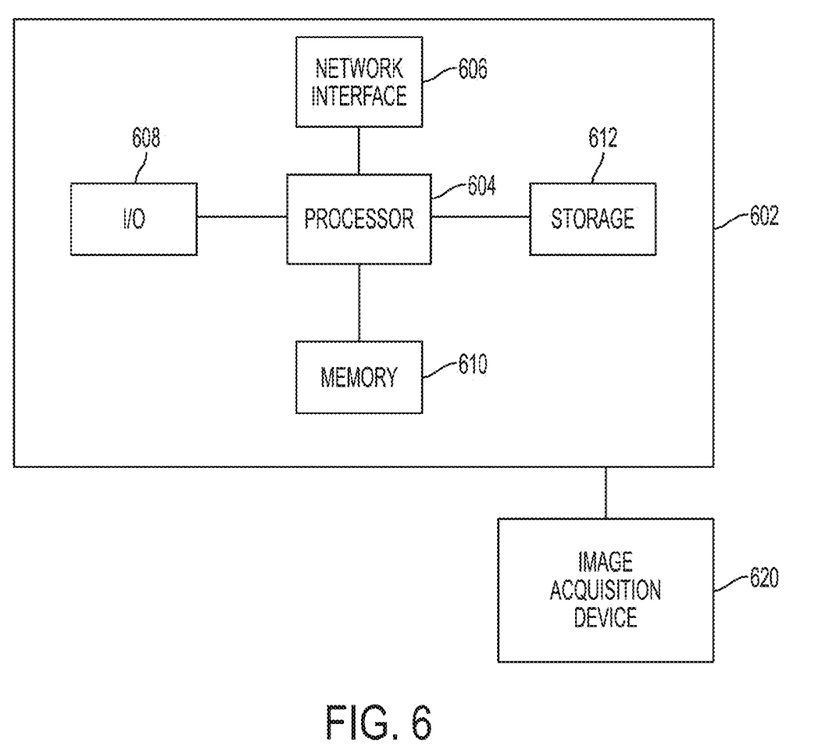
FIG. 6 is a high-level block diagram of a computer capable of implementing the present invention.

The above-described methods for non-invasive assessment of coronary artery disease may be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the methods of FIGS. 1 and 4 may be defined by the computer program instructions stored in the memory 610 and/or storage 612 and controlled by the processor 604 executing the computer program instructions. An image acquisition device 620, such as a CT scanning device, X-ray acquisition device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for assessment of coronary artery disease based on medical image data comprising:
   generating an anatomical model of a coronary artery from medical image data;
   estimating a velocity of blood in the coronary artery based on a spatio-temporal representation of contrast agent propagation over a length of the coronary artery in the medical image data, wherein estimating a velocity of blood in the coronary artery comprises:
     estimating a maximum velocity of blood on a cross-section of the coronary artery based on the spatio-temporal representation of contrast agent propagation over the length of the coronary artery in the medical image data, and
     mapping the maximum velocity of the blood on the cross-section of the coronary artery to an average velocity representing a spatial average of a velocity profile over the cross-section of the coronary artery using patient-specific mapping parameters; and
   simulating blood flow in the anatomical model of the coronary artery using a computational fluid dynamics (CFD) simulation using the estimated velocity of the blood in the coronary artery as a boundary condition.

2. The method of claim 1, wherein the medical image data comprises 4D medical image data, and the step of generating an anatomical model of a coronary artery from medical image data comprises:
   generating a 4D anatomical model of the coronary artery from 4D medical image data.

3. The method of claim 2, wherein the step of generating a 4D anatomical model of the coronary artery from 4D medical image data comprises:
   segmenting a coronary artery of interest in each of a plurality of frames of the 4D medical image data; and
   generating a 3D model of the segmented coronary artery of interest in each of the plurality of frames of the 4D medical image data.

4. The method of claim 1, wherein the step of estimating a maximum velocity of blood on a cross-section of the coronary artery based on a spatio-temporal representation of contrast agent propagation over a length of the coronary artery in the medical image data comprises:
   generating the spatio-temporal representation of contrast agent propagation over the length of the coronary artery based on time-intensity curves extracted from the medical image data; and
   estimating a slope of the spatio-temporal representation of contrast agent propagation for each point in the medical image data over the length of the coronary artery.

5. The method of claim 4, wherein the step of generating the spatio-temporal representation of contrast agent propagation over the length of the coronary artery based on time-intensity curves extracted from the medical image data comprises:
mapping an inverted intensity magnitude of points in the medical image data over the length of the coronary artery over time.

6. The method of claim 1, wherein the step of simulating blood flow in the anatomical model of the coronary artery using a computational fluid dynamics (CFD) simulation using the estimated velocity of the blood in the coronary artery as a boundary condition comprises:
solving Navier-Stokes equations constrained by the anatomical model of the coronary artery with the estimated velocity of the blood as an inlet velocity boundary condition.

7. The method of claim 1, wherein the step of simulating blood flow in the anatomical model of the coronary artery using a computational fluid dynamics (CFD) simulation using the estimated velocity of the blood in the coronary artery as a boundary condition comprises:
simulating pressure and velocity values over the coronary artery over time.

8. The method of claim 1, further comprising:
calculating one or more hemodynamic parameters based on the CFD simulation.

9. The method of claim 8, wherein the one or more hemodynamic parameters comprise at least one of flow rate, pressure drop, and wall-shear stress.

10. The method of claim 8, wherein the one or more hemodynamic parameters comprises at least one of coronary flow reserve (CFR) and fractional flow reserve (FFR).

11. The method of claim 1, wherein the medical image data comprises a sequence of computed tomography (CT) data.

12. The method of claim 1, wherein the medical image data comprises a sequence of X-ray angiography data.

13. The method of claim 1, wherein the medical image data comprises a sequence of rotational angiography data.

14. The method of claim 1, wherein mapping the maximum velocity of the blood on the cross-section of the coronary artery to an average velocity representing a spatial average of a velocity profile over the cross-section of the coronary artery using patient-specific mapping parameters comprises:
mapping the maximum velocity on the cross-section of the coronary artery to the average velocity representing the spatial average of the velocity profile over the cross-section of the coronary artery using patient-specific mapping parameters determined using a series of CFD simulations having various prescribed flow values and various simulated maximum and average velocity values.

15. The method of claim 1, wherein mapping the maximum velocity of the blood on the cross-section of the coronary artery to an average velocity representing a spatial average of a velocity profile over the cross-section of the coronary artery using patient-specific mapping parameters comprises:
calculating the average velocity representing the spatial average of the velocity profile over the cross-section of the coronary artery as $$V_{avg} = V_{max} \frac{(1+pW^q)}{2},$$

where $V_{avg}$ is the average velocity, $V_{max}$ is the maximum velocity, p and q are the patient-specific mapping parameters, and $$W = R\sqrt{\frac{f\rho}{\mu}},$$

where f is a frequency of the pulsatile flow, R is a cross-sectional area of the cross-section of the coronary artery, $\rho$ is the density of blood, and $\mu$ the dynamic viscosity of blood.

16. The method of claim 15, wherein the patient-specific parameters p and q are determined using a series of CFD simulations having various prescribed flow values, various values for one or more of W, f, R, $\rho$, or $\mu$, and various simulated maximum and average velocity values.

17. An apparatus for assessment of coronary artery disease based on medical image data comprising:
means for generating an anatomical model of a coronary artery from medical image data;
means for estimating a velocity of blood in the coronary artery based on a spatio-temporal representation of contrast agent propagation over a length of the coronary artery in the medical image data, wherein the means for estimating a velocity of blood in the coronary artery comprises:
means for estimating a maximum velocity of blood on a cross-section of the coronary artery based on the spatio-temporal representation of contrast agent propagation over the length of the coronary artery in the medical image data,
means for mapping the maximum velocity of the blood on the cross-section of the coronary artery to an average velocity representing a spatial average of a velocity profile over the cross-section of the coronary artery using patient-specific mapping parameters; and
means for simulating blood flow in the anatomical model of the coronary artery using a computational fluid dynamics (CFD) simulation using the estimated velocity of the blood in the coronary artery as a boundary condition.

18. The apparatus of claim 17, wherein the means for estimating a maximum velocity of blood on a cross-section of the coronary artery based on a spatio-temporal representation of contrast agent propagation over a length of the coronary artery in the medical image data comprises:
means for generating the spatio-temporal representation of contrast agent propagation over the length of the coronary artery based on time-intensity curves extracted from the medical image data; and
means for estimating a slope of the spatio-temporal representation of contrast agent propagation for each point in the medical image data over the length of the coronary artery.

19. The apparatus of claim 18, wherein the means for generating the spatio-temporal representation of contrast agent propagation over the length of the coronary artery based on time-intensity curves extracted from the medical image data comprises:
means for mapping an inverted intensity magnitude of points in the medical image data over the length of the coronary artery over time.

20. The apparatus of claim 17, wherein the means for simulating blood flow in the anatomical model of the coronary artery using a computational fluid dynamics (CFD) simulation using the estimated velocity of the blood in the coronary artery as a boundary condition comprises:

means for solving Navier-Stokes equations constrained by the anatomical model of the coronary artery with the estimated velocity of the blood as an inlet velocity boundary condition.

21. The apparatus of claim 17, further comprising:
means for calculating one or more hemodynamic parameters based on the CFD simulation.

22. The apparatus of claim 17, wherein the means for mapping the maximum velocity of the blood on the cross-section of the coronary artery to an average velocity representing a spatial average of a velocity profile over the cross-section of the coronary artery using patient-specific mapping parameters comprises:
means for mapping the maximum velocity on the cross-section of the coronary artery to the average velocity representing a spatial average of a velocity profile over the cross section of the coronary artery using patient-specific mapping parameters determined using a series of CFD simulations having various prescribed flow values and various simulated maximum and average velocity values.

23. A non-transitory computer readable medium encoded with computer executable instructions for assessment of coronary artery disease based on medical image data, the computer executable instructions defining steps comprising:
generating an anatomical model of a coronary artery from medical image data;
estimating a velocity of blood in the coronary artery based on a spatio-temporal representation of contrast agent propagation over a length of the coronary artery in the medical image data, wherein estimating a velocity of blood in the coronary artery comprises:
estimating a maximum velocity of blood on a cross-section of the coronary artery based on the spatio-temporal representation of contrast agent propagation over the length of the coronary artery in the medical image data, and
mapping the maximum velocity of the blood on the cross-section of the coronary artery to an average velocity representing a spatial average of a velocity profile over the cross-section of the coronary artery using patient-specific mapping parameters; and
simulating blood flow in the anatomical model of the coronary artery using a computational fluid dynamics (CFD) simulation using the estimated velocity of the blood in the coronary artery as a boundary condition.

24. The non-transitory computer readable medium of claim 23, wherein the computer executable instructions defining the step of estimating a maximum velocity of blood on a cross-section of the coronary artery based on a spatio-temporal representation of contrast agent propagation over a length of the coronary artery in the medical image data comprise computer executable instructions defining the steps of:
generating the spatio-temporal representation of contrast agent propagation over the length of the coronary artery based on time-intensity curves extracted from the medical image data; and
estimating a slope of the spatio-temporal representation of contrast agent propagation for each point in the medical image data over the length of the coronary artery.

25. The non-transitory computer readable medium of claim 24, wherein the computer executable instructions defining the step of generating the spatio-temporal representation of contrast agent propagation over a length of the coronary artery based on time-intensity curves extracted from the medical image data comprise computer executable instructions defining the step of:
mapping an inverted intensity magnitude of points in the medical image data over the length of the coronary artery over time.

26. The non-transitory computer readable medium of claim 23, wherein the computer executable instructions defining the step of simulating blood flow in the anatomical model of the coronary artery using a computational fluid dynamics (CFD) simulation using the estimated velocity of the blood in the coronary artery as a boundary condition comprise computer executable instructions defining the step of:
solving Navier-Stokes equations constrained by the anatomical model of the coronary artery with the estimated velocity of the blood as an inlet velocity boundary condition.

27. The non-transitory computer readable medium of claim 23, further comprising computer executable instructions defining the step of:
calculating one or more hemodynamic parameters based on the CFD simulation.

28. The non-transitory computer readable medium of claim 23, wherein mapping the maximum velocity of the blood on the cross-section of the coronary artery to an average velocity representing a spatial average of a velocity profile over the cross-section of the coronary artery using patient-specific mapping parameters comprises:
mapping the maximum velocity on the cross-section of the coronary artery to the average velocity representing a spatial average of a velocity profile over the cross section of the coronary artery using patient-specific mapping parameters determined using a series of CFD simulations having various prescribed flow values and various simulated maximum and average velocity values.

* * * * *